US012599453B2

(12) United States Patent
McKenzie

(10) Patent No.: US 12,599,453 B2
(45) Date of Patent: Apr. 14, 2026

(54) ORAL EXPANSION DEVICE

(71) Applicant: Charles McKenzie, Mesa, AZ (US)

(72) Inventor: Charles McKenzie, Mesa, AZ (US)

( * ) Notice: Subject to any disclaimer, the term of this patent is extended or adjusted under 35 U.S.C. 154(b) by 237 days.

(21) Appl. No.: 18/117,118

(22) Filed: Mar. 3, 2023

(65) Prior Publication Data

US 2023/0270518 A1     Aug. 31, 2023

Related U.S. Application Data

(63) Continuation-in-part of application No. 17/306,748, filed on May 3, 2021, now Pat. No. 11,896,438.

(60) Provisional application No. 63/019,572, filed on May 4, 2020.

(51) Int. Cl.
A61B 90/00 (2016.01)

(52) U.S. Cl.
CPC .................................... A61B 90/02 (2016.02)

(58) Field of Classification Search
CPC ....... A61B 90/02; A61B 17/24; A61B 17/663; A61B 1/24; A61B 17/0206; A61C 7/10; A63B 23/032; A61H 2205/026; A61H 1/02; A61M 29/00
See application file for complete search history.

(56) References Cited

U.S. PATENT DOCUMENTS

| | | | |
|---|---|---|---|
| 5,035,420 A * | 7/1991 | Beeuwkes, III | ..... A63B 23/032 |
| | | | 482/11 |
| 6,413,231 B1 * | 7/2002 | Berman | ............... A63B 23/032 |
| | | | 482/11 |
| 2007/0287598 A1 * | 12/2007 | Christensen | ............. A61H 1/02 |
| | | | 482/11 |

* cited by examiner

*Primary Examiner* — Brigid K Byrd
(74) *Attorney, Agent, or Firm* — Accelerate IP LLC

(57) ABSTRACT

An oral expansion device comprises a first body, main body and a second body wherein the first body and second body are attached to a body and a first tube and a second tube wherein the first tube and second tube having one end attached to the body and having a second end attached to an inflation device. The first tube can be attached internally to the first cavity to the inflate or deflate it and the second tube can be attached internally to the second cavity to inflate or deflate it. The body is manufactured from a flexible material. The first cavity and the second cavity can be manufactured from an inflatable material. The first cavity is an oval and the second cavity is a rectangular shape. The body has a 35-degree bend wherein the second cavity is centered on the 35-degree bend and the body can have two depressions on its sides.

13 Claims, 11 Drawing Sheets

SECTION A-A

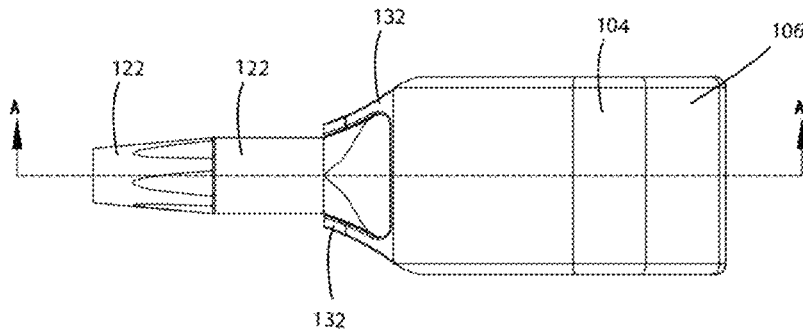
*FIG. 9a*
*FIG. 9b*
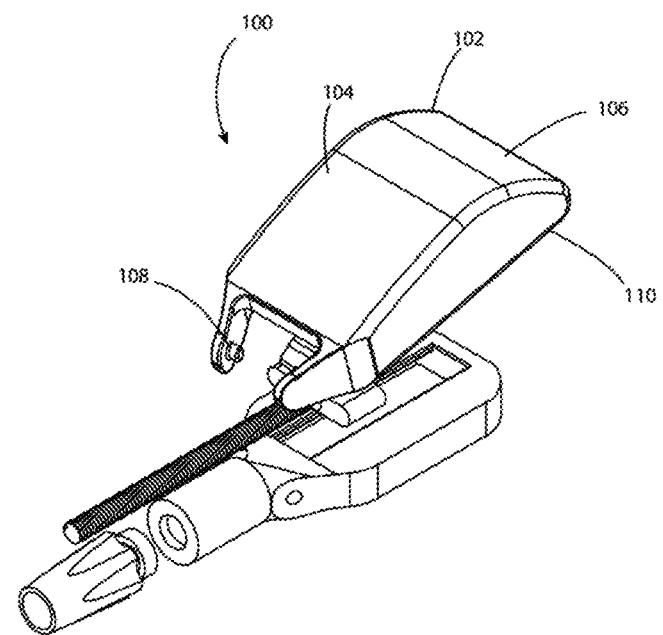
*FIG. 10*

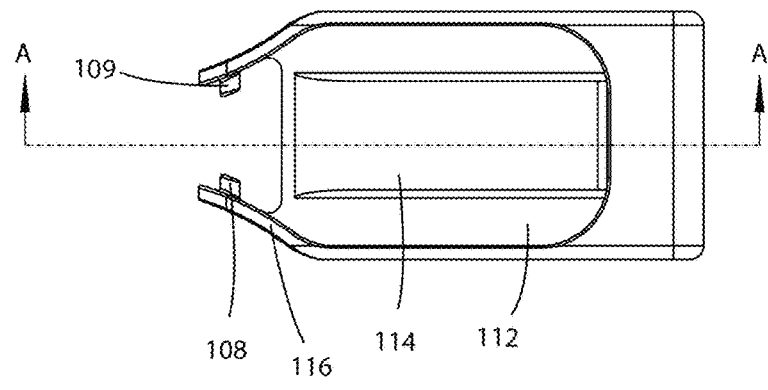
FIG. 11a
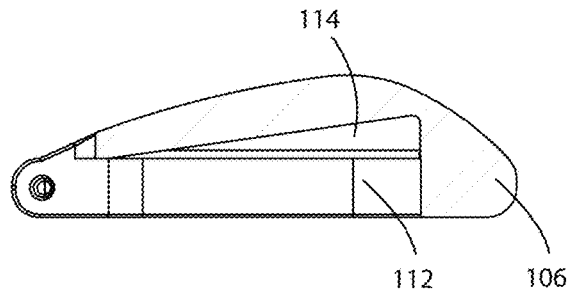
FIG. 11b
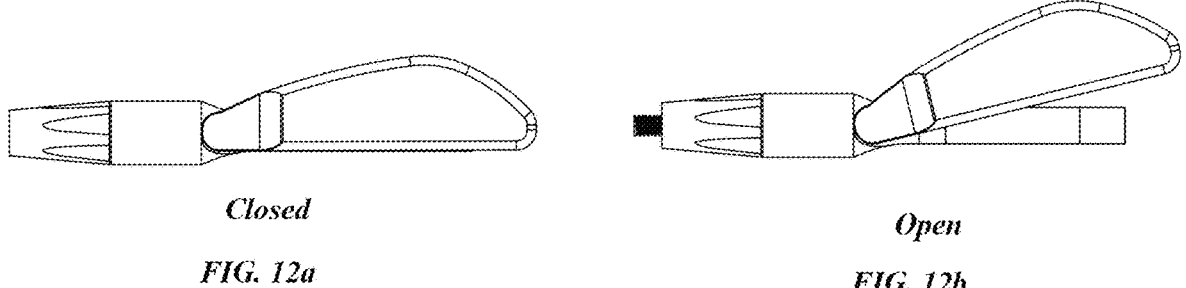
*Closed*
FIG. 12a
*Open*
FIG. 12b

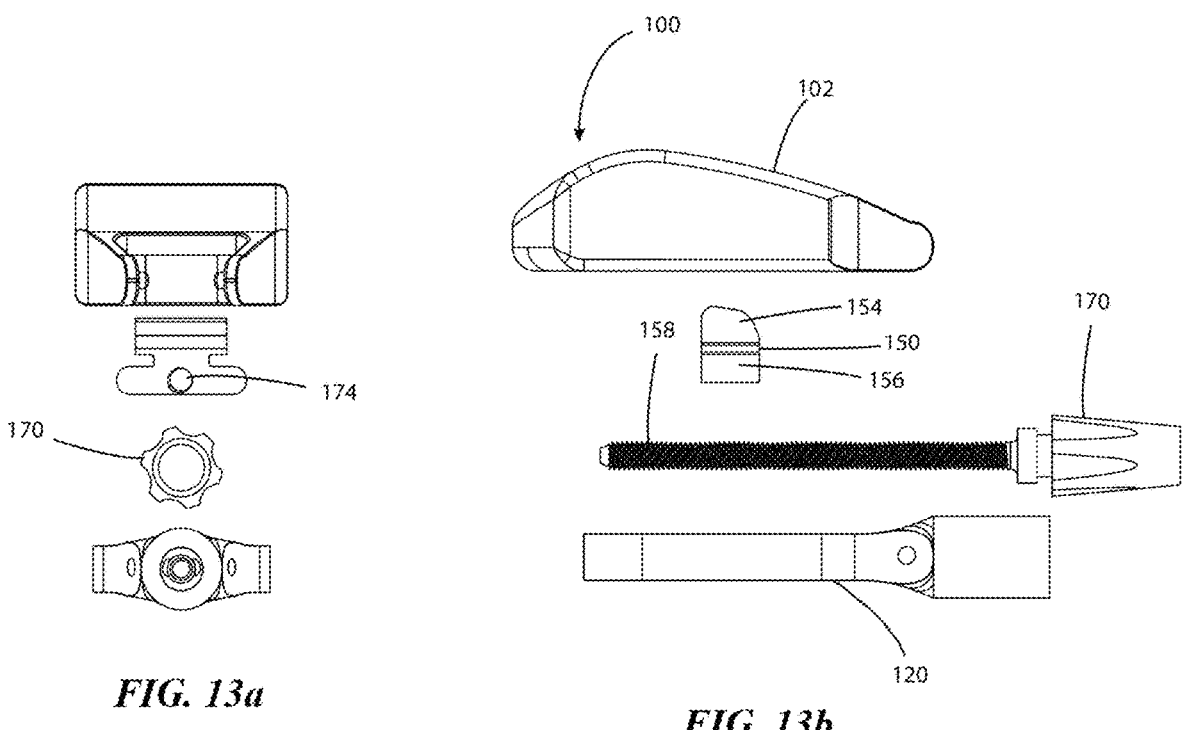
FIG. 13a
FIG. 13b
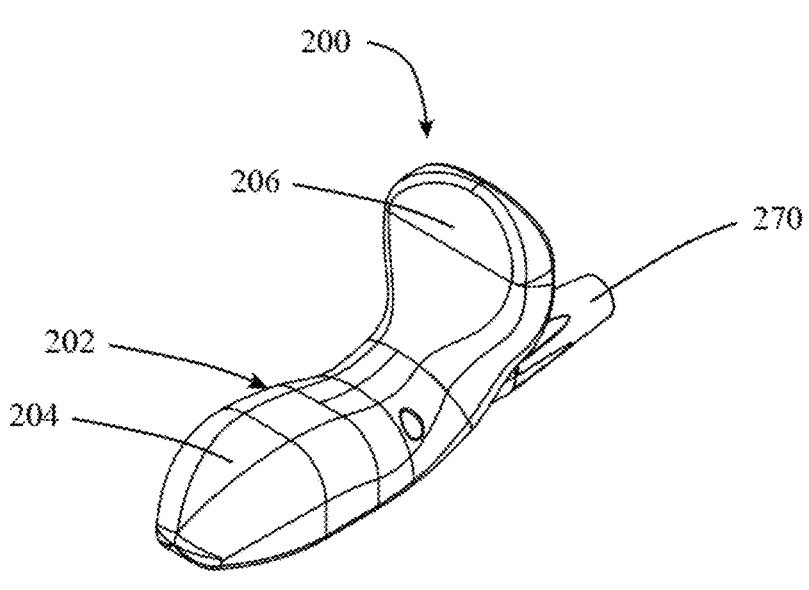
FIG. 14

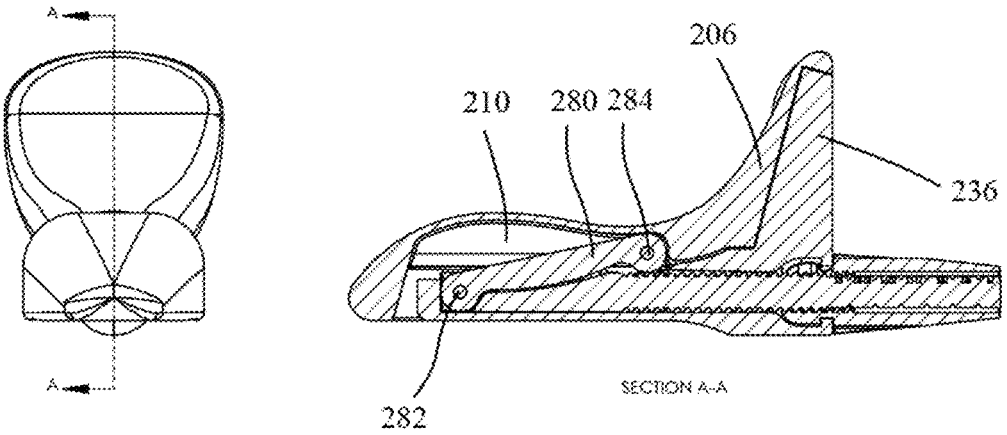
FIG. 17a                    FIG. 17b
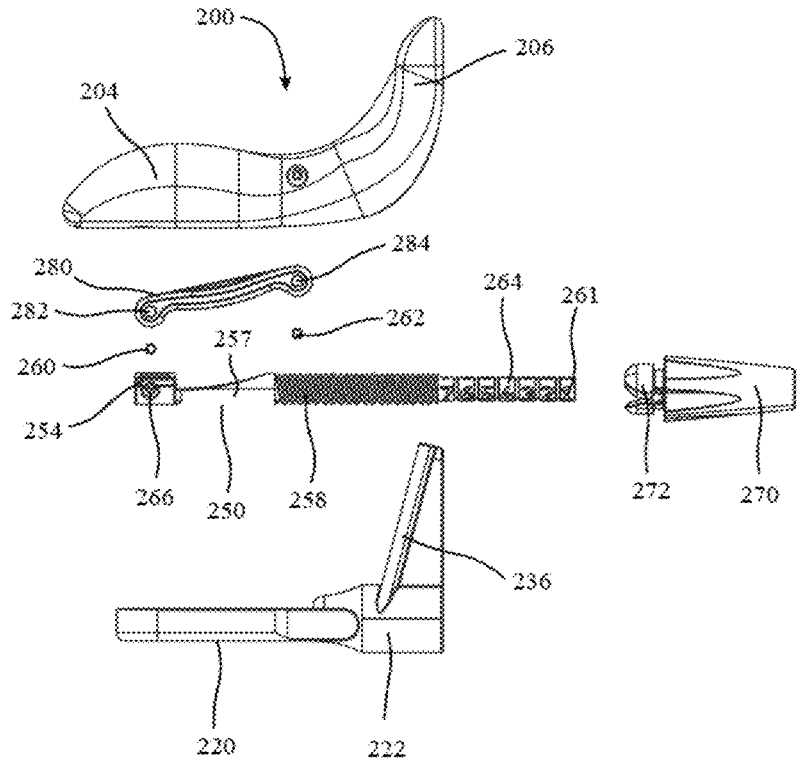
FIG. 18

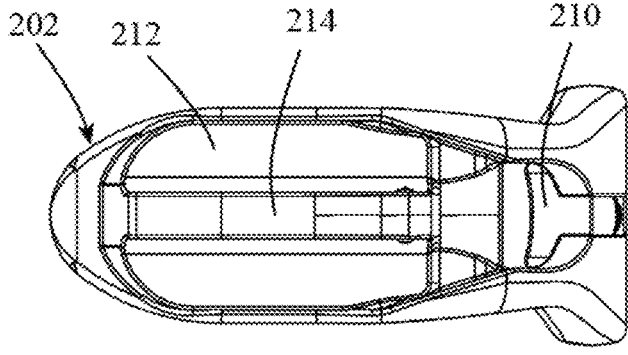
FIG. 20
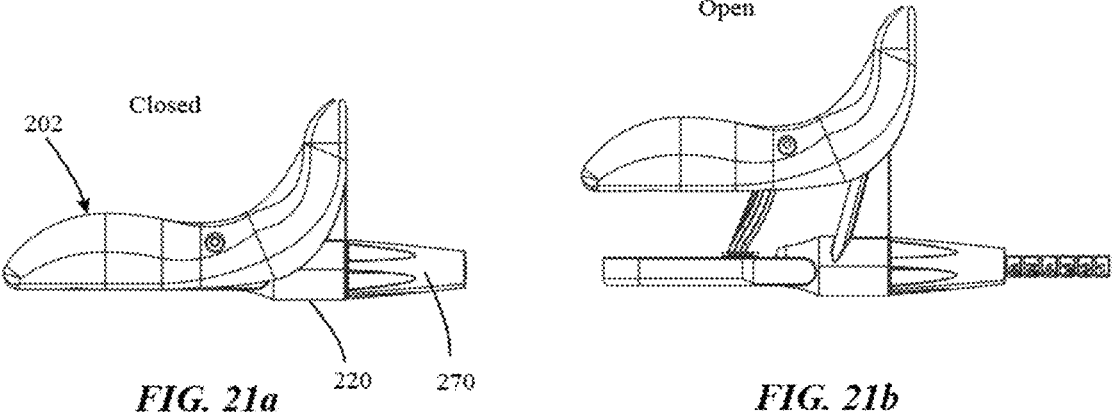
FIG. 21a    FIG. 21b

ORAL EXPANSION DEVICE

CROSS REFERENCE TO RELATED APPLICATION

This continuation in part application claims benefit from currently pending U.S. Nonprovisional application Ser. No. 17/306,748 titled "Oral Expansion Device" and having a filing date of May 3, 2021, all of which is incorporated by reference herein.

FIELD OF THE INVENTION

The present specification relates to an oral device, more particularly an oral expansion device for stretching skin on the face of a patient.

BACKGROUND OF THE INVENTION

The utility of skin grafts is the mainstay for wound care management. When receiving a skin graft the patient's skin can become tight and uncomfortable for the patient. Therefore, there is a need for device to stretch the skin as it heals to allow for flexibility and movement. Current methods of stretching the skin involve placing the patient's or another individual's thumbs in the patient's mouth and pushing outward on the lips and cheek. This method produces an inconsistent pressure and is not uniform across all surface area in the mouth. Furthermore, prior art devices include rubber bands that are placed in the corners of the patient's mouth which provides tension that is placed on the corners of the mouth to stretch the lip from side to side. This type of device only works for the patient's lips and does not provide any pressure to the cheeks.

Therefore, there is a need for a device that provides a consistent uniform surface pressure over the cheek and lip area of the patients mouth and that allows the patient to track his/her progress during the treatment.

BRIEF SUMMARY OF THE INVENTION

In embodiment an oral expansion device for a patient having teeth and skin with an inner surface inside the patient's mount, the device comprising a main body that can be inserted into the patient's mouth between the teeth and the inner surface. A first body detachably coupled to the main body, wherein the first body has an outside surface that mechanically or through changes in pressure expands to press against the inner surface and stretch the patient's skin. The change in pressure is caused by a second body having an outer surface wherein the first body and the second body can inflate and deflate by a pump. The pump is a manual or powered pump. The first body mechanically expands by operating a knob rotatably attached to the main body wherein the knob moves a rod that is connected to an expansion member and wherein as the knob turns the rod is rotated and the expansion member moves forward and aft within the main body.

The main body can further comprise a first member contacting a second member wherein the first member tapers out towards the second member wherein the first body is connected to the main body at a pivot point. The rod can be a threaded rod. The main body can have a sliding slot wherein an expansion member is slidable within the sliding slot as the knob rotates the rod. The first body can cover the main body when in its closed position. The first body has a second slot wherein the expansion member pushes against a second slot pushing the first body outward moving the first body into its open position pushing against the patient's skin wherein the second slot is at an angle allowing the first body to raise and lower as the expansion device is moved forward and aft within the main body. The change in pressure can be caused by a first tube and a second tube which are connected to the first body and the second body wherein the first tube and second tube opposing ends are connected to the pump which inflates or deflates the first body and the second body. The main body can be manufactured from biocompatible materials that form to the patient's mouth. The first body and main body can be manufactured from material such as plastic, polyvinyl, TPU, rubber or polymer. The first body and second body can be manufactured from material such as polyvinyl, TPU, rubber or polymer.

In embodiments a method of expanding a patient's skin using an oral expansion device comprising inserting the oral expansion device into the patient's mouth. Pushing against the patient's skin by a mechanical or pressurization expansion mechanism. Monitoring the patient's progress by the turns or how much pressure is applied to the oral expansion device.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the. Absent such clear statements of intent to apply a "special" definition, it is the inventor's intent and desire that the simple, plain, and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112 (f). Thus, the use of the words "function," "means" or "step" in the Detailed Description or Description of the Drawings or claims is not intended to somehow indicate a desire to invoke the special provisions of 35 U.S.C. § 112 (f), to define the invention. To the contrary, if the provisions of 35 U.S.C. § 112 (f) are sought to be invoked to define the inventions, the claims will specifically and expressly state the exact phrases "means for" or "step for", and will also recite the word "function" (i.e., will state "means for performing the function of molding a . . . , without also reciting in such phrases any structure, material or act in support of the function. Thus, even when the claims recite a "means for performing the function of molding a . . . , step for performing the function of molding a . . . ," if the claims also recite any structure, material or acts in support of that means or step, or that perform the recited function, then it is the clear intention of the inventors not to invoke the provisions of 35 U.S.C. § 112 (f). Moreover, even if the provisions of 35 U.S.C. § 112 (f) are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

Additional features and advantages of the present specification will become apparent to those skilled in the art upon consideration of the following detailed description of the illustrative embodiment exemplifying the best mode of carrying out the invention as presently perceived.

BRIEF DESCRIPTION OF THE DRAWINGS

These and other features, aspects, and advantages of the present specification will become better understood with regard to the following description, appended claims, and accompanying drawings where:

FIG. 9a is a top view of another embodiment of the oral expansion device in accordance to one, or more embodiments;

FIG. 9b is a cross-sectional side view of FIG. 9a of another embodiment of the oral expansion device in accordance to one, or more embodiments;

FIG. 10 is an exploded isometric view of another embodiment of the oral expansion device in accordance to one, or more embodiments;

FIG. 11a is a bottom view of the first body of another embodiment of the oral expansion device in accordance to one, or more embodiments;

FIG. 11b is a cross-sectional view of FIG. 11a of the first body of another embodiment of the oral expansion device in accordance to one, or more embodiments;

FIG. 12a is a side view of another embodiment of the oral expansion device in its open and closed position in accordance to one, or more embodiments;

FIG. 12b is a side view of another embodiment of the oral expansion device in its open position in accordance to one, or more embodiments;

FIG. 13a is an exploded front and side view of another embodiment of the oral expansion device in accordance to one, or more embodiments;

FIG. 13b is an exploded side view of another embodiment of the oral expansion device in accordance to one, or more embodiments;

FIG. 14 is an isometric view of another embodiment of the oral expansion device in accordance to one, or more embodiments;

FIG. 17a is a front view of another embodiment of the oral expansion device in accordance to one, or more embodiments;

FIG. 17b is a cross-sectional view of another embodiment of the oral expansion device in accordance to one, or more embodiments;

FIG. 18 is an exploded side view of another embodiment of the oral expansion device in accordance to one, or more embodiments;

FIG. 20 is a bottom view of the first body of another embodiment of the oral expansion device in accordance to one, or more embodiments;

FIG. 21a is a side view in its closed position of another embodiment of the oral expansion device in accordance to one, or more embodiments; and FIG. 21b is a side view in its open position of another embodiment of the oral expansion device in accordance to one, or more embodiments.

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Figure 1:
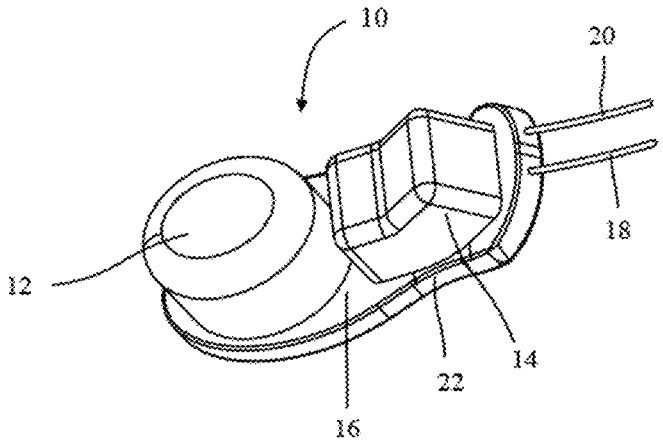
FIG. 1 is an isometric view of the oral expansion device in accordance to one, or more embodiments.
Figure 2:
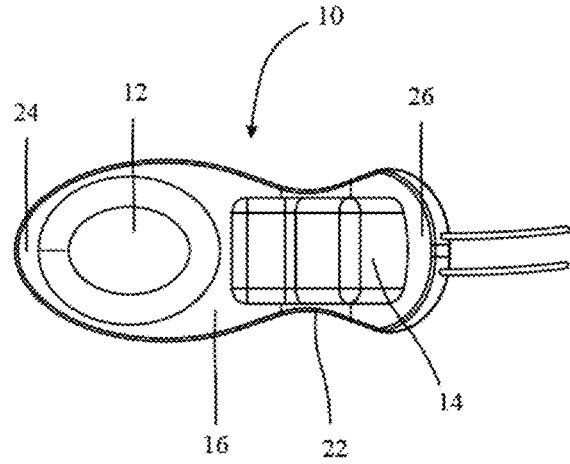
FIG. 2 is a top view of the oral expansion device in accordance to one, or more embodiments.
Figure 3:
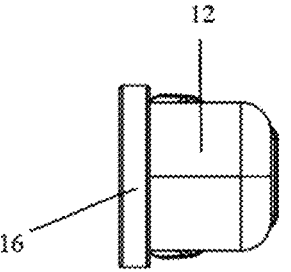
FIG. 3 is a side view of the oral expansion device in accordance to one, or more embodiments.
Figure 4:
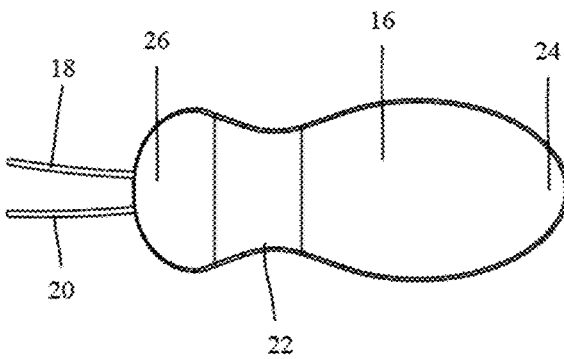
FIG. 4 is a bottom view of the oral expansion device in accordance to one, or more embodiments.
Figure 5:
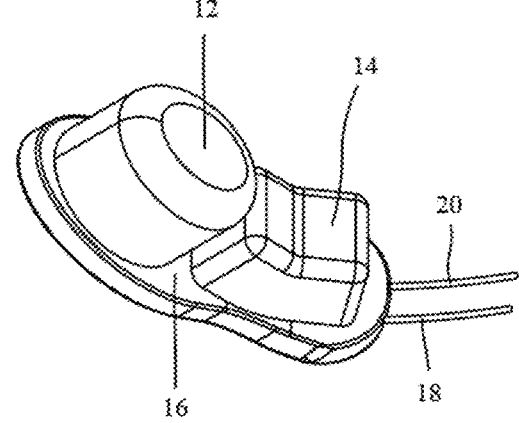
FIG. 5 is an isometric view of the oral expansion device in accordance to one, or more embodiments.

Referring initially to FIGS. 1-5, an oral expansion device for a patient having teeth and skin with an inner surface inside the patient's mouth shown generally at 10. An oral expansion device 10 can comprise a first body 12 and a second body 14 wherein the first body and second body can be attached to a main body 16 wherein the main body can be inserted into the patient's mouth between the teeth and the inner surface. The main body 16 can be manufactured from semi-rigid material and can flex when inserted into a patient's mouth. A first tube 18 and a second tube can have one end attached to or integrate within the main body 16 wherein the first tube can be connected internally to the first body 12, and the second tube can be connected internally to the second body 14, the first tube and second tube's second end can be attached to a inflation/deflation device thus causing a change in pressure against the patient's cheek. The main body 12 can have a length of such as, for example, between 40 mm and 100 mm, more preferably a length of between 50 mm and 80 mm, and still more preferably a width of approximately 70 mm or the like. The main body 12 can have a width of such as, for example, between 10 mm and 70 mm, more preferably a length of between 20 mm and 50 mm, and still more preferably a width of approximately 30 mm or the like. The main body 12 can have a thickness of such as, for example, between 1 mm and 15 mm, more preferably a length of between 3 mm and 10 mm, and still more preferably a width of approximately 5 mm or the like.

The main body 12 can further comprise two depressions 22 wherein each depression can be approximate to or on the angle where the patient's mouth rests. The two depressions 22 can retain the oral expansion device 10 in the patient's mouth. The main body 12 can have a forward portion 24 and aft portion 26 wherein the forward portion and aft portion can be shaped like such as, for example, conical, parabolic, ogive, cone or the like. The aft portion 26 can accept the first tube 18 and the second tube 20 wherein the first tube and the second tube can be sealed against the aft portion creating an airtight seal. The main body 12 can further comprise a 35-degree bend at about 40 mm to 60 mm from the forward portion 24, and about 10 mm to 30 mm from the aft portion 26.

Figure 6:
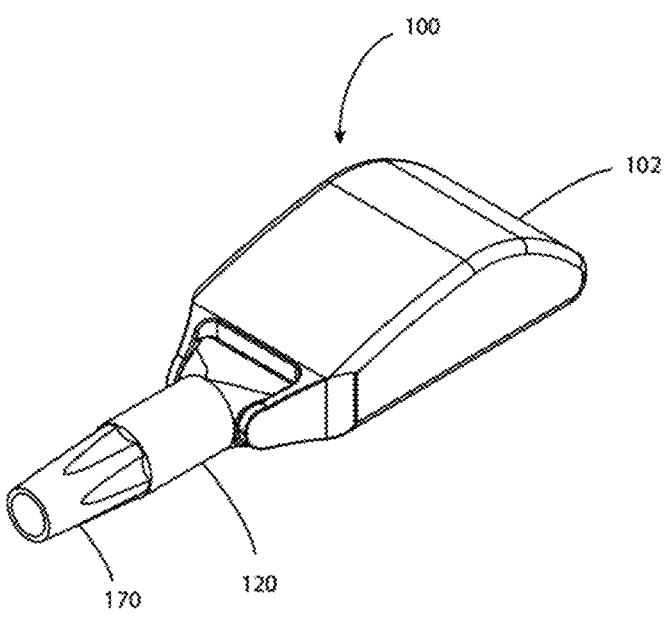
FIG. 6 is an isometric view of another embodiment of the oral expansion device in accordance to one, or more embodiments.
Figure 7:
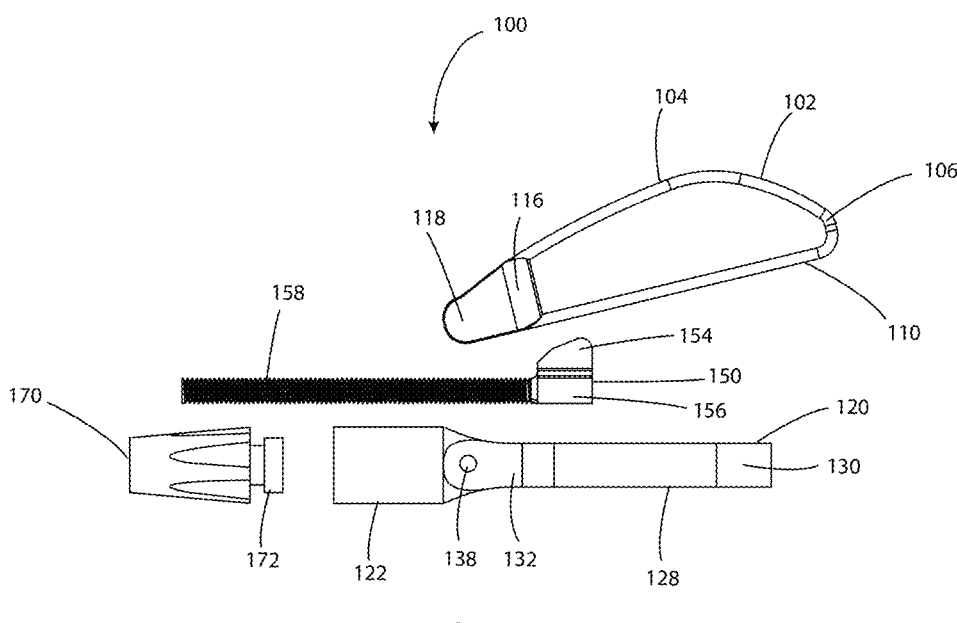
FIG. 7 is an exploded side view of another embodiment of the oral expansion device in accordance to one, or more embodiments.
Figure 8:
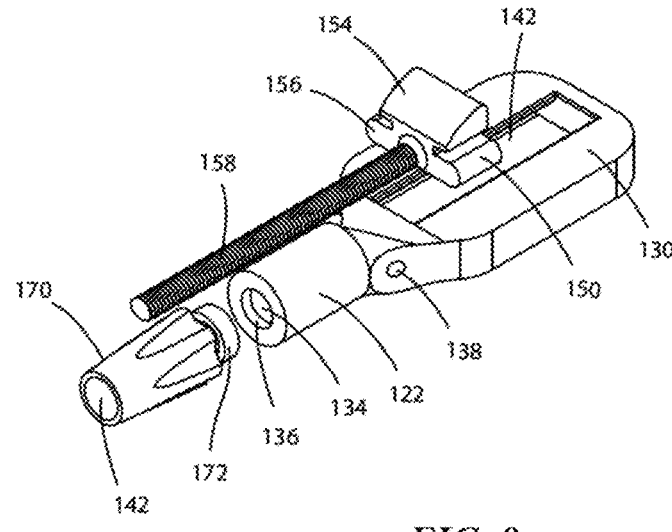
FIG. 8 is an exploded isometric view omitting the first body of another embodiment of the oral expansion device in accordance to one, or more embodiments.

The first body 12 can be placed on the main body 12 wherein the first body's shape can be such as, for example, oval, circular, rectangular, triangular or the like, and can be placed towards the forward portion of the main body. The second body 14 can be placed on the main body 12 and centered on the 35-degree bend or can be approximate to the 35-degree bend wherein the second body's shape can be such as, for example, oval, circular, rectangular, triangular or the like. The first body 12 and second body 14 can be manufactured from material that can inflate and deflate such as, for example, polyvinylchloride, nylon, polyethylene, composite polyethylene, polyester, or the like. A pressurization expansion mechanism can expand the first body 12 and the second body 14 can be inflated or deflated by the pressurization system which can be a manual or power pump with fluid or air. The first body 12 can be placed all of the way in the patient's mouth wherein the first body can be placed against the cheek and the main body placed against the teeth. The first body 12 can expand the patient's cheek outward away from the teeth thus stretching the skin of a burn victim or an individual in need oral stretching. The first body 12 can be detachably coupled to the main body 12, wherein the first body has an outside surface that mechanically, as shown in FIGS. 6-11, or through changes in pressure expands to press against the inner surface and stretch the patient's skin.

The second body 14 and/or first body 12 can be placed partially in the mouth of the patient wherein the second body and/or first body can expand outward away from the teeth when air, fluid or gas is applied to the first body and the second body stretching the cheek in an outwardly direction. The first body 12 and the second body 14 can inflate or deflate in increments which can gradually stretch the outer surface of the patient's mouth, cheeks and lips as the pressure is applied to the inside of the mouth against the cheek and lips pushing the opposite direction on the patient's teeth. The patient can track his/her progress by tracking how much air, gas or fluid is put into the first body 12 and the second body 14. In certain embodiments the first body 12 and the second body 14 can each be inflated and deflated by itself, or both can be inflated and deflated at the same time.

Referring to FIGS. 6-11, shows another embodiment including a mechanical expansion mechanism of an oral expansion device 100. The oral expansion device 100 can have a first body 102 and a main body 120 wherein the first body is detachably coupled to the main body. The first body 102 can comprise an outer surface 104 and an inner surface 110 wherein the outer surface can be shaped like an ellipse having an outer edge 106 that chamfers into a radius for easy insertion into a patient's mouth. In certain embodiments the outer surface 104 shape can be such as, for example, an egg-shape, round, eccentric, or the like. The main body 120 can have a first member 122 and a second member 130 wherein the first member can transition into the second member by a second taper 132 wherein the first member can taper or gradually increase in size out into a second member 130. The second member 130 can have a top surface 126 and a bottom surface 128 and can be substantially shaped like a rectangle with radiused corners and in other embodiments the second member can be shaped like a circle, square, hexagon, or the like. The first member 122 can be substantially circular in shape and can extend from the second member 130.

The second member 130 can have a sliding slot 124 wherein the sliding slot can be substantially centered on the second member wherein the slot can be a t-slot, or in other embodiments the slot can be a dovetail slot or the like. The sliding slot 124 can extend from one end of the second member 130 to the transition area of the second member to the first member. The first member 122 can have a thru hole 134 that can have an inner lip 136 wherein the first thru hole can extend from the front of the first member 122 to the sliding slot 124. The second taper 132 can further comprise a second thru hole 138 wherein the second thru hole can extend from one side of the second taper to the other side or in other embodiments the second thru hole can be a blind hole that does not penetrate the first thru hole 134 going through the first member 122.

The first body 102 can have a first taper 116 that matches the profile of the second taper 132 wherein the first taper can extend from the first body 102 wherein the first taper can have a third slot 142 wherein the slot forms two mirrored protrusions 118 that protrude from the first body wherein the protrusions 108 have matching pins 109 on the inner side of both protrusions. The inner surface 110 can be substantially flat and can have a first slot 112 and a second slot 114 as shown in FIG. 11 wherein the first slot allows for the first body to accept and cover the sliding member 124 of main body 120. The second slot 114 can be substantially the same length as the first slot 112 wherein the second slot is at an angle wherein the angle can be such as, for example, between 1 and 45 degrees, more preferably between 5 and 25 degrees, and still more preferably approximately 10 degrees or the like.

The oral expansion device 100 can further comprise an expansion member 150 wherein the expansion member can comprise an expansion body 152 having an upper portion 154 and a lower portion 156 wherein the lower portion is in the shape of a "T" and the upper portion has an angle can be the substantially the opposite of the second slot. Wherein the upper portion 154 can push against the second slot 114 raising the first body 102 at its pivot point away from the main body 120. The expansion member 150 can further comprise a rod 158 having threads wherein the rod extends from the lower portion. The rod 158 can be all thread, screw, bolt, threaded rod, or the like. The first slot 112 can have the substantially same shape as the second member 130 wherein when the first body is in its closed position as shown in FIG. 12 it can be substantially cover the second member. The first body 102 can be attached to the main body 120 by the protrusions 108 and the second thru hole 138 wherein the first body can pivot on the protrusions and second thru hole's axis.

The oral expansion device 100 can further comprise a knob 170 wherein the knob can have an outer lip 172 wherein the outer lip can be contained by the inner lip 136 of the second body. The mechanical expansion mechanism can use the knob 170 which can comprise a threaded portion 174 wherein as the knob rotates about its axis the threaded portion can pull or push the rod 158 which can move forward or aft the expansion member and can either push or release the first body 102 within the third slot 142 away from the main body 120. In other embodiments, as shown in FIG. 13 the rod 158 can extend form the knob and the threaded portion can be on the expansion member 150 wherein the expansion member can slide within the third slot 142 as the knob and rod rotate.

Figure 15:
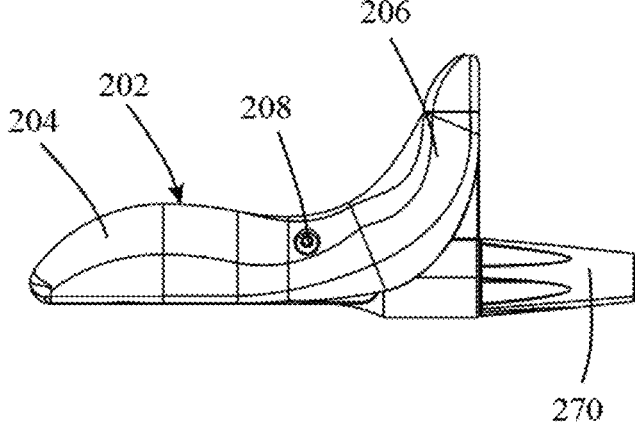
FIG. 15 is a side view of another embodiment of the oral expansion device in accordance to one, or more embodiments.
Figure 16:
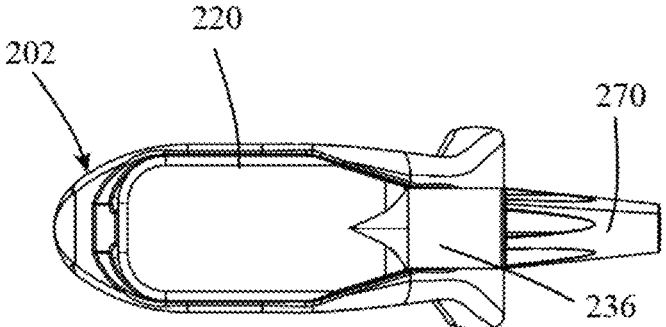
FIG. 16 is a bottom view of another embodiment of the oral expansion device in accordance to one, or more embodiments.
Figure 19:
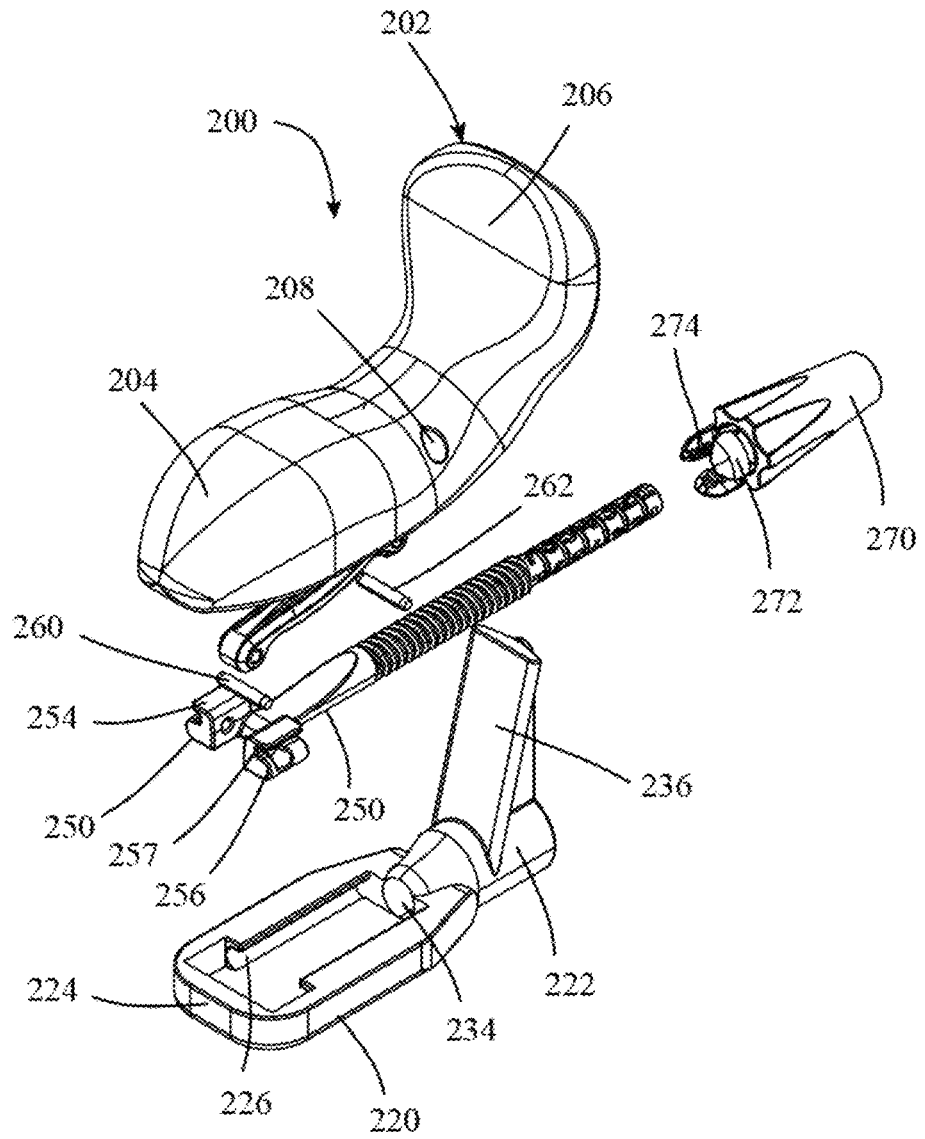
FIG. 19 is an exploded isometric view of another embodiment of the oral expansion device in accordance to one, or more embodiments.

Referring to FIGS. 14-20 in certain embodiments an oral expansion device 200 for a patient having teeth and skin with an inner surface inside the patient's mouth the device comprising a main body 220 and a first body 202 that can be inserted into the patient's mouth between the teeth and the inner surface. A lever arm 280 wherein the lever arm is coupled to the first body 202 and to an expansion member 250 wherein the expansion member is slidably coupled to the main body 220 and coupled to a knob 270. The knob 270 can be rotatably coupled to the main body 220.

The first body 202 can comprise an outer surface 204 and an upper protrusion 206 and a first pivot joint 208. The first body 202 can be any suitable shape, but in the preferred embodiment the shape is shown in FIG. 14. The first body 202 can have an inner slot 210 wherein when in its closed position the lever arm 280 can sit within the inner slot as shown in FIG. 17b. The first body 202 can have the upper protrusion extending from its outer surface 204 wherein the outer surface and protrusion can be the shape and size of at least one of the individual's inner cheek, lips, teeth or the like. The first body 202 can be connected to the lever arm 280 by the first pivot joint 208 and the lever arm's second connection point 284 by a second pin 262 wherein the lever arm can rotate about the second pin. The first body 202 can further comprise a first guide 212 that can be on the backside of the upper protrusion 206.

The main body 220 can comprise a first member 222 and a second member 224 wherein the first member has a first hole 234 which can couple to the knob and allows the expansion member 250 to move axially within the first hole. The first member 222 can have a second guide 236 protruding from the first member. The second guide 236 can be an integral to the first member 222 wherein the first body 202 can freely slide on the second guide wherein the first guide 212 can fully or partially surround the second guide allowing the first body to slide freely on the second guide's linear line.

The second member 224 can have a first slot 226 wherein the first slot can be at least one of such as, for example slot, groove, channel, or the like. The first body 202 can encompass or surround the upper portion of the main body 220 within the inner slot 210 leaving the bottom of the main body and outer surface 204 of the first body exposed to at least one of the user's mouth, teeth, lip, inner cheek or the like. The first body 202 and the main body 220 can be sized to fit in such as, for example, a baby, youth, teen or adults' mouth.

The expansion member 250 can comprise an upper portion 254 and a lower portion 256 wherein the lower portion has at least one pivot joint 266. The upper portion 254 and the lower portion 256 can form a guide 257 which can be captured by and slide within the first slot 226. The upper portion 254 and the lower portion 256 can be integral or coupled to a transition 257 wherein the transition extends and is coupled or integral to a rod 258 which can extend from the transition. A marking rod 264 can extend from the rod 258 wherein the marking rod can be coupled to or integral to the threaded rod. The rod 258 can be threaded and can be any suitable thread and pitch size. The marking rod 264 can have at least one number etched into it and at least one line etched into the outer diameter allowing the user to measure in inches, millimeter, centimeter or the like the distance moved when turning the knob 270 and moving the first body away from the main body.

The lever arm 280 can have a first connection point 282 and a second connection point 284 wherein the first connection point can be coupled to the expansion member 250 at the pivot joint 266 with a first pin 260 and the second connection point 284 can be coupled to the first body 202 at its first pivot joint 208—by a second pin 262. The knob 270 can be rotatably coupled to the first member by an outer support 272 wherein the outer support can have an inner thread 274 on its inner diameter. The threaded rod 258 can be coupled to the inner threads 724 wherein the as the knob rotates the expansion member 250 moves in and out within the sliding slot 226. The outer support 272 can be tabs or the like wherein the outer support can be rotatably coupled to the first member 222. In the preferred embodiment the thread and pitch size of the inner thread 274 can match the thread and pitch size of a pitch on the threaded rod 258.

Referring to FIGS. 21a and 21b the oral expansion device 200 can be mechanically opened and closed in a closed state or an open state pushing against at least one of the individual's inner cheek, lips, teeth or the like. As the knob 270 rotates it the expansion member 250 can push or pull against the lever arm 280 which in turns pushes against the first body 202 sliding the first body on the main body 220. The main body can be manufactured from biocompatible materials that form to the patient's mouth. The first body and main body are manufactured from material such as plastic, polyvinyl, TPU, rubber or polymer. The first body and second body are manufactured from material such as polyvinyl, TPU, rubber or polymer In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only and is not intended to limit the scope of the present disclosure, which is defined solely by the claims. Accordingly, embodiments of the present disclosure are not limited to those precisely as shown and described.

Certain embodiments are described herein, including the best mode known to the inventors for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

What is claimed is:

1. An oral expansion device for a patient having a mouth, teeth with a front side, and facial skin having an inner surface inside the patient's mouth, the device comprising:

a main body having a main body axis, a substantially flat teeth side, and a main body inner side opposite the teeth side;

a first body adjacent to the main body inner side having a first body inner side and a substantially contoured cheek side opposite the first body inner side; and a lever arm having a first end pivotally coupled to the first body and a second end pivotally coupled to an expansion member at a pivot joint wherein the expansion member is slidably coupled to the main body such that turning a knob moves the pivot joint along the main body axis to selectively extend the first body away from the main body from a closed position to an extended position;

wherein the first body expands the distance between the patient's teeth and the inner surface inside the patient's mouth when the device is in the patient's mouth and is expanded from the closed position to the extended position.

2. The oral expansion device according to claim 1, wherein the first body is coupled to the lever arm at has a first pivot joint.

3. The oral expansion device according to claim 2, wherein the lever arm and the expansion member are manufactured from at least one material selected from polyvinyl, TPU, rubber or polymer.

4. The oral expansion device according to claim 1, wherein the expansion member has an upper portion and a lower portion wherein the upper portion and the lower portion form a guide.

5. The oral expansion device according to claim 1, wherein the first body mechanically expands by operating the knob which is rotatably coupled to the main body wherein the knob is rotatably coupled to a threaded portion of a rod wherein rotation of the knob causes the rod to move linearly, wherein the rod is connected to the expansion member such that as the rod moves linearly the expansion member moves forward and aft within the main body.

6. The oral expansion device according to claim 5, wherein the main body can further comprise an upper portion coupled to a lower portion forming a guide wherein the first body is connected to the main body by the lever arm and the expansion member.

7. The oral expansion device according to claim 6, wherein the first body covers the main body when the first body is in the closed position.

8. The oral expansion device according to claim 6, wherein the first body is rotatably connected to the lever arm by a first pivot joint wherein the expansion member pushes against the lever arm wherein the first body moves outward into an open position configured to push against the patient's skin wherein the main body comprises a second guide set at an angle allowing the first body to slide on the second guide allowing the first body to raise and lower as the expansion member pushes or pulls against the lever arm and is moved forward and aft within the main body.

9. The oral expansion device according to claim 5, wherein the main body has a sliding slot wherein the expansion member is slidable within the sliding slot as the knob rotates and linearly moves the rod.

10. The oral expansion device according to claim 1, wherein the main body is manufactured from biocompatible materials configured to form to the patient's mouth.

11. The oral expansion device according to claim 1, wherein the first body and the main body are manufactured from material from at least one of plastic, polyvinyl, TPU, rubber or polymer.

12. The oral expansion device according to claim 1, wherein the first body extends away from the main body in a first direction and a rod couples the expansion member to the knob, and wherein the rod extends from the expansion member in a second direction that is substantially orthogonal to the first direction.

13. The oral expansion device according to claim 1, wherein the expansion member moves axially relative to the main body, and a rod couples the expansion member to the knob and extends from the expansion member in the direction of the expansion member's movement.

* * * * *